(12) United States Patent
Xiang et al.

(10) Patent No.: US 6,923,958 B2
(45) Date of Patent: Aug. 2, 2005

(54) DNA VACCINES ENCODING CEA AND A CD40 LIGAND AND METHODS OF USE THEREOF

(75) Inventors: Rong Xiang, San Diego, CA (US); Ralph A. Reisfeld, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 201 days.

(21) Appl. No.: 10/090,238

(22) Filed: Mar. 2, 2002

(65) Prior Publication Data

US 2003/0176377 A1 Sep. 18, 2003

(51) Int. Cl.[7] ............................ A01N 48/00; C12P 19/34; C12N 15/79; C12N 15/75
(52) U.S. Cl. .................. 424/93.2; 424/93.1; 424/93.21; 424/234.1; 424/69.3; 424/69.5; 435/230.1; 435/91.1; 435/69.1; 435/69.3; 435/69.5; 514/44; 536/23.1; 536/23.5
(58) Field of Search ........................... 514/44; 536/23.1, 536/23.5; 424/93.1, 201.1, 85.1; 435/476, 69.1, 69.3, 69.5, 320.1, 252.3, 252.31

(56) References Cited

U.S. PATENT DOCUMENTS

| | | | |
|---|---|---|---|
| 5,939,400 A | 8/1999 | Steinman et al. | |
| 6,086,891 A | 7/2000 | Hurwitz et al. | |
| 6,147,055 A | 11/2000 | Hobart et al. | |
| 6,207,646 B1 | 3/2001 | Kreig et al. | |
| 6,214,804 B1 | 4/2001 | Felgner et al. | |
| 6,235,523 B1 | 5/2001 | Gajewczyk et al. | |

FOREIGN PATENT DOCUMENTS

| | | | |
|---|---|---|---|
| CA | 2250428 | | 5/1997 |
| WO | WO 99/43839 A1 | * | 9/1999 |
| WO | WO 02/03961 A1 | | 1/2002 |

OTHER PUBLICATIONS

Xiang et al. J. Immunol. 2001, vol. 167, pp. 4560–4565.*
Rong Xiang, et al., Clinical Cancer Research, vol. 7, pp. 856s–864s (Mar. 2001) (Suppl.).
James W. Hodge, et al., Cancer Research, vol. 59, pp. 5800–5807 (Nov. 15, 1999).
Erik Kass, et al., Cancer Research, vol. 59, pp. 676–683 (Feb. 1, 1999).
Stephen D. Gillies, et al., Journal of Immunology, pp. 6195–6203 (1998).
Joanne P. McLaughlin, et al., Cancer Research, vol. 56, pp. 2361–2367 (May 15, 1996).
Shin Sasaki, et al., Nature Biotechnology, vol. 19, pp. 543–547 (Jun. 2001).
Nicholas P. Restifo, Nature Biotechnology, vol. 19, pp. 527–528 (Jun. 2001).
Wolfgang W. Leitner, et al., Cancer Research, vol. 60, pp. 51–55 (Jan. 1, 2000).
N.P. Restifo, et al., Gene Therapy, vol. 7, pp. 89–92, (2000).
Andreas G. Niethammer, et al., Nature Medicine, vol. 8 (12), pp. 1369–1375 (Dec., 2002).

* cited by examiner

Primary Examiner—James Housel
Assistant Examiner—Bao Qun Li
(74) Attorney, Agent, or Firm—Olson & Hierl, Ltd.

(57) ABSTRACT

A DNA vaccine effective for eliciting an immune response against cells that present a carcinoembryonic antigen (CEA) comprises a DNA operably encoding a CEA and a DNA operably encoding a CD40 ligand, SEQ ID NO:1 and SEQ ID NO: 2, respectively, or its homotrimer, CD40LT. The DNA vaccine can be incorporated in a delivery vector such as an attenuated live bacterium or virus, or a liposome carrier. In a method embodiment, the DNA vaccine is administered orally to a mammal, such as a human, to elicit an immune response against CEA presenting cells such as colon cancer cells. A preferred method embodiment includes the additional step of treating the mammal with recombinant antibody fusion protein huKS1/4-IL2 to enhance the immune response effectiveness of the vaccine.

15 Claims, 9 Drawing Sheets

FIGURE 7

Human CEA gene, DNA
SEQ. ID NO.: 1

```
gagctcctca cacggactct gtcagctcct ccctgcagcc tatcggccgc ccacctgagg      60
cttgtcggcc gcccacttga ggcctgtcgg ctgccctctg caggcagctc ctgtcccta     120
caccccctcc ttccccgggc tcagctgaaa gggcgtctcc cagggcagct ccctgtgatc     180
tccaggacag ctcagtctct cacaggctcc gacgcccct atgctgtcac ctcacagccc     240
tctcattacc attaactcct cagtcccatg aagttcactg agcgcctgtc tcccggttac     300
acgaaaactc tgtgacaggg accacgtctg tcctgctctc tgtggaatcc cagggcccag     360
ccagtgcctg cacggaaca gatgctccat aaatactggt taaatgtgtg ggagatctct     420
aaaagaaac atatccactc cgtgtggccc ccagcagtca gagtctgttc catgtggaca     480
cagggcact ggcaccagca tgggaggagg ccagcaagtg cccgcggctg cccaggaat     540
gacgcctcaa cccccagagc ttcagaaggg aggacagagg cctgcaggga atagatcctc     600
ccgcctgacc ctgcagccta atcctgagtt cagggtcagc tcacaccacg tcgaccctgg     660
tcagcatccc tagggcagtt ccagacaagg ccggaggtct cctcttgccc tccaggggt     720
gacattgcac acagacatca ctcaggaaac ggattcccct ggacaggaac ctggctttgc     780
taaggaagtg gaggtggagc ctggtttcca tccttgctc caacagaccc ttctgatctc     840
tcccacatac ctgctctgtt cctttctggg tcctctgagg acctgttctg ccagggtcc     900
ctgtgcaact ccagactccc tcctggtacc accatgggga aggtggggtg atcacaggac     960
actcagcctc gcagagacag agaccaccca ggactgtcag ggagaacatg gacaggccct    1020
gagccgcagc tcagccaaca gacacggaga gggagggtcc cctggagcc ttccccaagg    1080
acagcagagc ccagagtcac ccacctccct ccaccacagt cctctctttc caggacacac    1140
aagacacctc ccctccaca tgcaggatct ggggactcct gagacctctg ggcctgggtc    1200
tccatccctg ggtcagtggc ggggttggtg gtactggaga cagagggctg gtccctcccc    1260
acccaccacc cagtgagcct ttttctagcc cccagagcca cctctgtcac cttctgttg    1320
gccatcatcc cccttccca gagccctgga gagcatgggg agacccggga cctgctggt    1380
ttctctgtca caaaggaaaa taatcccct ggtgtgacag acccaaggac agaacacagc    1440
acaggtcagc actggggaaa gacaggttgt ccacagggga tgggggtcca tccaccttgc    1500
ccaaaagatt tgtctgagga actgaaaata gaagggaaaa aagaggaggg acaaagagg    1560
cagaaatgag aggggagggg acagaggaca cctgaataaa gaccacaccc atgacccacg    1620
tcatgctgag aagtactcct gccctaggaa gagactcagg gcagaggag gaaggacagc    1680
acaccagaca gtcacagcag ccttgacaaa acgttcctgg aactcaagct cttctccaca    1740
gaggaggaca gagcagacag cagagaccat ggagtctccc tggcccctc cccacagatg    1800
gtgcatcccc tggcagaggc tcctgctcac aggtgaaggg aggacaaccc ctgggagagg    1860
gtgggaggag ggagcacaga gactggctgg ggtctcctgg gtaggacagg gctgtgagac    1920
gcacagaggg ctcctgttgg agcctgaata gggaagagga catcagagag ggacaggagt    1980
cacaccagaa aatcaaatt gaactggaat tggaaagggg caggaaaacc taagagttc    2040
tattttccta gttaattgtc actggccact acgtttttaa aaatcataat aactgcatca    2100
gatgacactt taaataaaaa cataaccagg gcatgaaaca ctgtcctcat ccgcctaccg    2160
cggacattgg aaaataagcc ccaggctgtg gagggccctg ggaaccctca tgaactcatc    2220
cacaggaatc tgcagcctgt cccaggcact gggtgcaacc aagatcacac aaatccctgc    2280
cctcatgaag ctcatgctct catgggagg aagacagaca tacaaagaga tctagaatgt    2340
gaggtcaggt gttgacaaga gcctgggagg aatagagcag ggaaaggtca gaaaaggaag    2400
acccaaggtc tctagaggag gtgtcaggga agggatctcc caagaatgcc ctgatgtgag    2460
caggacctga aggcaatggg gagggagccg tgaagacccc tggaaaagca gattccacac    2520
agggaaatgc caaggtcgga ggtgctaagg aaataggaga cacactgctg accttgacct    2580
actaggacac acacacacac acacacacac actcactcac tccagggctg ggggatgaag    2640
agacctgctc aggacccagg acccattt tccaccctaa tgcataggtc caatattga    2700
ccgatgctct ctgctctctc ctagcctcac ttctaaccttc tggaacccg ccaccactg    2760
ccaagctcac tattgaatcc acgccgttca atgtcgcaga ggggaaggag gtgcttctac    2820
ttgtccacaa tctgccccag catcttttgt gctacagctg gtacaaaggt gaaagagtgg    2880
atggcaaccg tcaaattata ggatatgtaa taggaactca acaagctacc ccagggcccg    2940
catacagtgg tcgagagata atatacccca atgcatccct gctgatccag aacatcatcc    3000
agatgacac aggattctac accctcacg tcataaagtc agatcttgtg aatgaagaag    3060
caactggcca gttccggta taccgtgagt gattccccca tgacctctgg gtgttgggg    3120
tcagttctac ttcccacaca caggattatc aggcctgggc tgtgctgtgg cccctctgc    3180
attacgaacc atgttagggt ttgggcattt agtgcaggat acacacagaa gagacaaact    3240
tcaacagatc agaattcctt tccggcatcc agaccctgca g                        3281
```

FIGURE 8

Human CD40L, DNA
SEQ ID NO.: 2

```
ccatttcaac tttaacacag catgatcgaa acatacaacc aaacttctcc ccgatctgcg      60
gccactggac tgcccatcag catgaaaatt tttatgtatt tacttactgt ttttcttatc     120
acccagatga ttgggtcagc acttttttgct gtgtatcttc atagaaggtt ggacaagata    180
gaagatgaaa ggaatcttca tgaagatttt gtattcatga aaacgataca gagatgcaac    240
acaggagaaa gatccttatc cttactgaac tgtgaggaga ttaaaagcca gtttgaaggc    300
tttgtgaagg atataatgtt aaacaaagag gagacgaaga agaaaacag ctttgaaatg    360
caaaaaggtg atcagaatcc tcaaattgcg gcacatgtca taagtgaggc cagcagtaaa    420
acaacatctg tgttacagtg ggctgaaaaa ggatactaca ccatgagcaa caacttggta    480
accctggaaa atgggaaaca gctgaccgtt aaaagacaag gactctatta tatctatgcc    540
caagtcacct tctgttccaa tcgggaagct tcgagtcaag ctccatttat agccagcctc    600
tgcctaaagt cccccggtag attcgagaga atcttactca gagctgcaaa tacccacagt    660
tccgccaaac cttgcaggca acaatccatt cacttgggag gagtatttga attgtaacca    720
ggtgcttcgg tgtttgtcaa tgtgactgat ccaagccaag tgagccatgg cactggctca    780
cgtcctttgg cttactcaaa ctctgaacag tgtcaccttg caggctgtgg tggagctga    839
```

FIGURE 9

Murine CD40L, DNA
SEQ ID NO.: 3

```
ctttcagtca gcatgataga aacatacagc caaccttccc ccagatccgt ggcaactgga      60
cttccagcga gcatgaagat ttttatgtat ttacttactg ttttcottat cacccaaatg     120
attggatctg tgcttttttgc tgtgtatctt catagaagat tggataaggt cgaagaggaa     180
gtaaaccttc atgaagattt tgtattcata aaaaagctaa agagatgcaa caaaggagaa     240
ggatctttat ccttgctgaa ctgtgaggag atgagaagc aatttgaaga ccttgtcaag      300
gatataacgt taaacaaaga agagaaaaaa gaaaacagct tgaaatgca agaggtgat       360
gaggatcctc aaattgcagc acgttgta agcgaagcca acagtaatgc agcatccgtt       420
ctacagtggg ccaagaaagg atattatacc atgaaaagca acttggtaat gcttgaaaat     480
gggaaacagc tgacggttaa aagagaagga ctctattatg tctacactca agtcaccttc     540
tgctctaatc gggagccttc gagtcaacgc ccattcatcg tcggcctctg gctgaagccc     600
agcagtggat ctgagagaat cttactcaag gcggcaaata cccacagttc ctcccagctt     660
tgcgagcagc agtctgttca cttgggcgga gtgtttgaat tacaagctgg tgcttctgtg     720
tttgtcaacg tgactgaagc aagccaagtg atccacagag ttggcttctc atcttttggc     780
ttactcaaac tctgaacagt gcgctgtcct aggctgcagc agggctgatg ctggcagtct     840
tccctataca gcaagtcagt taggacctgc cctgtgttga actgcctatt tataaccta      900
ggatcctcct catggagaac tatttattat gtaccoccaa ggcacataga gctggaataa     960
gagaattaca gggcaggcaa aaatcccaag ggaccctgct ccctaagaac ttacaatctg    1020
aaacagcaac cccactgatt cagacaacca gaaagacaa agccataata cacagatgac    1080
agagctctga tgaaacaaca gataactaat gagcacagtt ttgttgtttt atgggtgtgt    1140
cgttcaatgg acagtgtact tgacttacca gggaagatgc agaagggcaa ctgtgagcct    1200
cagctcacaa tctgttatgg ttgacctggg ctccctgcgg ccctagtagg              1250
```

DNA VACCINES ENCODING CEA AND A CD40 LIGAND AND METHODS OF USE THEREOF

GOVERNMENTAL RIGHTS

This invention was made with government support under Contract Nos. CA 83856 and CA 70320 by the National Institutes of Health. The government has certain rights in this invention.

FIELD OF THE INVENTION

This invention relates to deoxyribonucleic acid (DNA) vaccines. More particularly, this invention relates to DNA vaccines containing polynucleotide constructs encoding for carcinoembryonic antigen (CEA) and a CD40 ligand.

BACKGROUND OF THE INVENTION

Vaccines have been utilized to provide a long term protection against a number of disease conditions by very limited administration of a prophylactic agent that stimulates an organism's immune system to destroy disease pathogens before they can proliferate and cause a pathological effect. Various approaches to vaccines and vaccinations are described in Bernard R. Glick and Jack J. Pasternak, *Molecular Biotechnology, Principles and Applications of Recombinant DNA*, Second Edition, ASM Press pp. 253–276 (1998).

Vaccination is a means of inducing the body's own immune system to seek out and destroy an infecting agent before it causes a pathological response. Typically, vaccines are either live, but attenuated, infectious agents (virus or bacteria) or a killed form of the agent. A vaccine consisting of a live bacteria or virus must be non-pathogenic. Typically, a bacterial or viral culture is attenuated (weakened) by physical or chemical treatment. Although the agent is nonvirulent, it can still elicit an immune response in a subject treated with the vaccine.

An immune response is elicited by antigens, either specific macromolecules, or an infectious agent. These antigens are generally either proteins, polysaccharides, lipids, or glycolipids, which are recognized as "foreign" by lymphocytes known as B cells and T cells. Exposure of both types of lymphocytes to an antigen elicits a rapid cell division and differentiation response, resulting in the formation of clones of the exposed lymphocytes. B cells produce plasma cells, which in turn, produce proteins called antibodies (Ab), which selectively bind to the antigens present on the infectious agent, thus neutralizing or inactivating the pathogen (humoral immunity). In some cases, B cell response requires the assistance of CD4$^+$ helper T cells.

The specialized T cell clone that forms in response to the antigen exposure is a cytotoxic T lymphocyte (CTL), which is capable of binding to and eliminating pathogens and tissues that present the antigen (cell-mediated or cellular immunity). In some cases, an antigen presenting cell (APC) such as a dendritic cell, will envelop a pathogen or other foreign cell by endocytosis. The APC then processes the antigens from the cells, and presents these antigens in the form of a histocompatability molecule:peptide complex to the T cell receptor (TCR) on CTLs, thus stimulating an immune response.

Humoral immunity characterized by the formation of specific antibodies is generally most effective against acute bacterial infections and repeat infections from viruses, whereas cell-mediated immunity is most effective against viral infection, chronic intracellular bacterial infection, and fungal infection. Cellular immunity is also known to protect against cancers and is responsible for rejection of organ transplants.

Antibodies to antigens from prior infections remain detectable in the blood for very long periods of time, thus affording a means of determining prior exposure to a pathogen. Upon re-exposure to the same pathogen, the immune system effectively prevents reinfection by eliminating the pathogenic agent before it can proliferate and produce a pathogenic response.

The same immune response that would be elicited by a pathogen can also sometimes be produced by a non-pathogenic agent that presents the same antigen as the pathogen. In this manner, the subject can be protected against subsequent exposure to the pathogen without having previously fought off an infection.

Not all infectious agents can be readily cultured and inactivated, as is required for vaccine formation, however. Modern recombinant DNA techniques have allowed the engineering of new vaccines to seek to overcome this limitation. Infectious agents can be created that lack the pathogenic genes, thus allowing a live, nonvirulent form of the organism to be used as a vaccine. It is also possible to engineer a relatively nonpathogenic organism such as *E. coli* to present the cell surface antigens of a pathogenic carrier. The immune system of a subject treated with such a transformed carrier is "tricked" into forming antibodies to the pathogen. The antigenic proteins of a pathogenic agent can be engineered and expressed in a nonpathogenic species and the antigenic proteins can be isolated and purified to produce a "subunit vaccine." Subunit vaccines have the advantage of being stable, safe, and chemically well defined; however, their production can be cost prohibitive.

A new approach to vaccines has emerged in recent years, broadly termed genetic immunization. In this approach, a gene encoding an antigen of a pathogenic agent is operably inserted into cells in the subject to be immunized. The treated cells are transformed and produce the antigenic proteins of the pathogen. These in vivo-produced antigens then trigger the desired immune response in the host. The genetic material utilized in such genetic vaccines can be either a DNA or RNA construct. Often the polynucleotide encoding the antigen is introduced in combination with other promoter polynucleotide sequences to enhance insertion, replication, or expression of the gene.

DNA vaccines encoding antigen genes can be introduced into the host cells of the subject by a variety of expression systems. These expression systems include prokaryotic, mammalian, and yeast expression systems. For example, one approach is to utilize a viral vector, such as vaccinia virus incorporating the new genetic material, to innoculate the host cells. Alternatively, the genetic material can be incorporated in a vector or can be delivered directly to the host cells as a "naked" polynucleotide, i.e. simply as purified DNA. In addition, the DNA can be stably transfected into attenuated bacteria such as *Salmonella typhimurium*. When a patient is orally vaccinated with the transformed *Salmonella*, the bacteria are transported to Peyer's patches in the gut (i.e., secondary lymphoid tissues), which then stimulate an immune response.

DNA vaccines provide an opportunity to immunize against disease states that are not caused by traditional pathogens, such as genetic diseases and cancer. Typically, in a genetic cancer vaccine, antigens to a specific type of tumor cell must be isolated and then introduced into the vaccine.

One of the major obstacles for achieving a tumor-specific immune response is to overcome peripheral T cell tolerance against tumor self-antigens and induce cytotoxic T lymphocytes (CTLs), which effectively eradicate disseminated tumor metastases and subsequently maintain a long-lasting immunological memory preventing tumor recurrence. Human carcinoembryonic antigen (CEA) is an oncofetal membrane glycoprotein, which provides a relevant tumor self-antigen target for the development of DNA vaccines for immunotherapy. A useful animal model for CEA-based vaccines is reported by Clarke et al. Cancer Res. 1998, 58:1469. The model involves the establishment of a mouse line that carries the genomic DNA transgene for human CEA and expresses CEA in a tissue-specific manner similar to humans. Following in vivo priming with CEA-transfected fibroblasts, anti-CEA CD8$^+$ T cells have been elicited in these transgenic mice, which were tolerant to CEA in the CD4$^+$ T cell compartment, described by Mizobata et al. Cancer Immunol. Immuother. 2000, 49:285. Studies in humans by Tsang et al. J Nat'l Cancer Inst. 1995, 87:982, have indicated that CD8$^+$ CTLs specific for CEA are not negatively selected, similar to findings obtained with transgenic mice.

The biological roles of CD40 ligand (CD40L), particularly its interaction with CD40 expressed on antigen presenting cells during costimulation of T cell activation, are well known in the art. CD40 is a 48 kDa glycoprotein expressed on the surface of all mature B cells, most mature B-cell malignancies, and some early B-cell acute lymphocytic leukemias, but it is not expressed on plasma cells, Clark, Tissue Antigens 1990, 35:33–36. CD40L, a type II membrane protein of 35 kDa and a member of the tumor necrosis factor (TNF) gene family, is expressed on the surface of T cells upon antigen recognition. Members of the TNF family are biologically most active when expressed as homotrimers. CD40L is no exception in this regard and can be expressed as a homotrimer (CD40LT) by modification of a 33 amino acid leucine zipper motif fused to the N-terminus of the entire extracellular domain of this ligand. CD40LT DNA has been reported by Gurunathan et al. J. Immunol. 1998, 161:4563, to enhance cellular immune responses such as induction of IFN-$\gamma$ and cytolytic T cell activity when mice were vaccinated with DNA encoding the highly immunogenic model antigen $\beta$-galactosidase.

CD40L is critically involved in the activation of T cells necessary to induce an effective protective immunity against tumor self-antigens. Once MHC class I antigen:peptide complexes are taken up by dendritic cells (DCs) and presented to naive T cells, the first antigen signal is delivered via T cell receptors (TCR), followed by upregulation of CD40L. On the T cell surface, CD40L then induces costimulatory activity on DCs via CD40-CD40L interactions. Thus primed, these APCs now express costimulatory molecules B7.1 (CD80) and B7.2 (CD86), which send a second costimulatory signal to T cells via interaction with CD28, an event required for full activation of T cells to concurrently produce pro-inflammatory cytokines INF-$\gamma$ and IL12, and to perform effector functions.

An effective means of enhancing efficacy of DNA vaccines is to grow the plasmid encoding DNA in a non-replicating strain of Salmonella typhimurium, which can then be applied as an oral vaccine. The live, attenuated bacteria transport the DNA through the gastrointestinal tract and then through the M cells that cover the Peyer's patches of the gut. From there the attenuated bacteria enter APCs such as dendritic cells and macrophages, where they die, because of their mutation, liberating multiple copies of the DNA inside the phagocytes.

Attenuated bacteria are believed to provide a "danger signal" and stimulate the innate immune system, producing pro-inflammatory cytokines like IL12 and mediators such as nitric oxide that enhance antigen presentation and promote $T_H1$-type cellular immune responses associated with the eradication of tumors. In fact, attenuated S. typhimurium has been reported to be an effective carrier for an autologous oral DNA vaccine that protects against murine melanoma (Xiang et al. Proc. Nat Acad. Sci (USA) 2000, 97:5492). A recombinant Listeria monocytogenes vaccine was reported to be highly effective in mediating regression of primary murine melanoma and their established lung metastases (Pan et al. Cancer Res. 1999, 59:5254). L. monocytogenes produces a strong cellular immune response since, unlike most other intracellular bacteria, it escapes into the cytoplasm by disrupting the phagosomal membrane thus allowing any protein it secretes to target both MHC class I and class II pathways of the infected cell for antigen presentation.

Xiang et al., Clin. Cancer Res., 2001, 3:8565, reports on partial tumor-protection against a lethal challenge of MC38 murine colon carcinoma cells, stably transduced with CEA and KSA, a human pan-epithelial cell adhesion molecule. Mice were vaccinated by oral gavage with a CEA-based DNA vaccine carried by attenuated Salmonella typhimurium, which induced MHC class I antigen-restricted CD8$^+$ T cell responses, resulting in rejection of subcutaneous tumors. However, this occurred in only some of the experimental mice transgenic for CEA, even when boosted with a recombinant antibody-IL2 fusion protein that targeted IL2 to the tumor microenvironment.

There is an ongoing need for vaccines that elicit a CD8$^+$ T cell-mediated tumor-protective immune response against CEA self-antigen with improved efficacy against colon cancer. The present invention accomplishes this goal with a unique, dual function DNA vaccine encoding CEA and CD40LT, activating both DCs and naive T lymphocytes, particularly when aided by boosts with huKS1/4-IL2 fusion protein.

SUMMARY OF THE INVENTION

A vaccine that is effective against CEA presenting cells such as colon cancer cells is provided. The vaccine comprises a plasmid DNA encoding CEA (e.g., DNA sequence SEQ ID NO: 1) and a plasmid DNA encoding a CD40 ligand such as human CD40L, DNA sequence SEQ ID NO: 2 or its homotrimer CD40LT. The CEA and CD40L DNA, SEQ ID NO: 1 and SEQ ID NO: 2, respectively, can be incorporated in the same plasmid or in different plasmids. The combination of plasmid DNA encoding both CEA and a CD40 ligand in a single vaccine promotes activation of both naive T cells and antigen presenting cells such as dendritic cells, thus stimulating two different immune response systems.

The plasmid DNA of the vaccines of the present invention can be operably incorporated in an efficient carrier such as an attenuated bacterium, a non-replicating virus, or a liposome particle.

In a method aspect of the present invention, a DNA vaccine comprising a plasmid DNA encoding CEA (SEQ ID NO: 1) and a plasmid DNA encoding a CD40L (SEQ ID NO: 2) or its homotrimer CD40LT, is administered to a mammal, such as a human, in an amount effective for eliciting an immune response against CEA presenting cells such as colon cancer cells.

In another method aspect of the invention, a mammal such as a human is sequentially administered (a) a DNA vaccine comprising a plasmid DNA encoding CEA (SEQ ID NO: 1)

and a CD40 ligand (SEQ ID NO: 21) or its homotrimer CD40LT, in an amount effective for eliciting an immune response against CEA presenting cells such as colon cancer cells, and (b) an effective immune response enhancing amount of a recombinant antibody-IL2 fusion protein (huKS1/4-IL2). The huKS-1/4-IL2 fusion protein enhances the immune responsiveness of the mammal treated with the DNA vaccine so that the immune system more effectively attacks CEA presenting cells, such as colon cancer cells. The vaccine and fusion protein can be administered orally or parenterally. Preferably the vaccine is administered orally, and the fusion protein is administered intravenously.

The vaccines of the present invention provide a preventative treatment for cancers such as, for example, colon cancer, by eliciting an immune response against cells that present CEA, including colon cancer cells.

BRIEF DESCRIPTION OF THE DRAWINGS

In the Drawings.

FIG. 7 depicts the DNA sequence of a gene encoding for human CEA, SEQ ID NO: 1;

FIG. 8 depicts the DNA sequence encoding for human CD40 ligand, SEQ ID NO: 2.; and FIG. 9 depicts the DNA sequence encoding for murine CD40 ligand, SEQ ID NO: 3.

DETAILED DESCRIPTION OF PREFERRED EMBODIMENTS

Figure 1:
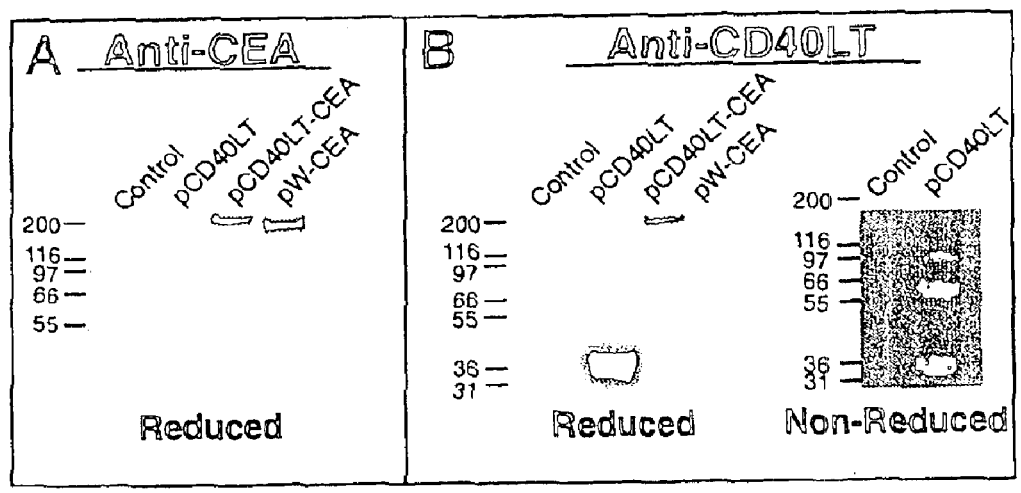
FIG. 1 depicts a Western blot analysis of lysed, transformed Cos-7 cells containing plasmid CEA and plasmid CD40LT, confirming the presence of both CEA and CD40LT DNA in the cells.

A DNA vaccine effective against CEA presenting cells such as certain cancer cells comprises a plasmid DNA construct encoding CEA (SEQ ID NO: 1) and a plasmid DNA encoding a CD40 ligand (SEQ ID NO: 2) or its homotrimer, CD40LT. The CEA and CD40L DNA, SEQ ID NO: 1 and SEQ ID NO: 2, respectively, can be incorporated in the same plasmid or in different plasmids. The DNA plasmid(s) can be operably incorporated into a carrier such as an attenuated bacterium, a non-reproducing virus, or a liposome particle. The DNA vaccine can also comprise "naked" DNA.

The DNA vaccines of the present invention stimulate formation of CTLs that are active against CEA presenting cells, such as colon cancer cells. Because CEA is a specific marker for colon cancer cells, a CTL that forms in response to the vaccine will substantially target only such cancer tissues. CD40 ligand stimulates dendritic cells, which are the most effective type of APCs that aid in producing a cellular immune response. A vaccine comprising a combination of DNA encoding CEA and a CD40 ligand, SEQ ID NO: 1 and SEQ ID NO: 2, respectively, can promote activation of naive T cells both directly and indirectly through the intervention of dendritic cells. Such a combination vaccine simultaneously stimulates two different immune response mechanisms, thus increasing the efficiency of the treatment.

As used herein, and in the appended claims, the term "DNA" refers to deoxyribonucleic acid in both the singular and plural grammatical forms. The term "immunity", as used herein, refers to long term immunological protection against the virulent form of the infectious agent. The term "immunization", as used herein, refers to prophylactic exposure to an antigen of a pathogenic agent derived from a non-virulent source and which results in immunity to the pathogen in the treated subject.

A DNA useful in the vaccines of the present invention preferably comprises a nucleotide sequence that encodes CEA (SEQ ID NO: 1) and/or a CD40 ligand (SEQ ID NO: 2), operably linked to regulatory elements needed for gene expression. Preferably the CD40 ligand is CD40LT. The CEA and CD40 ligand DNA, SEQ ID NO: 1 and SEQ ID NO: 2, respectively, are preferably incorporated in the vaccine as a single plasmid, designated herein as pCEA-CD40LT (i.e., plasmid CEA-CD40 LT). Alternatively, the vaccine can comprise a plasmid DNA encoding CEA (SEQ ID NO: 1) and a separate plasmid DNA encoding CD40L (SEQ ID NO: 2).

When taken up by a cell, a DNA molecule can remain present in the cell as a functioning extrachromosomal molecule and/or can integrate into the cell's chromosomal DNA. DNA can be introduced into cells in the form of a plasmid which can remain as separate genetic material. Alternatively, a linear DNA that can integrate into the chromosome can be introduced into the cell. When introducing DNA into a cell, reagents which promote DNA integration into chromosomes can be added, as is known in the art. DNA sequences that promote integration can also be included in the vaccine. DNA encoding CEA and a CD40 ligand, SEQ ID NO: 1 and SEQ ID NO: 2, respectively, can remain part of the genetic material in an attenuated live microorganism or recombinant microbial vector form of the vaccine, which can live in the cells of the patient.

Useful DNA vaccines preferably include regulatory elements necessary for expression of a nucleic acid molecule. Such elements include, for example, a promoter, an initiation codon, a stop codon, and a polyadenylation signal. In addition, enhancers are often required for expression of a sequence that encodes an immunogenic target protein. As is known in the art, these elements are preferably operably linked to the sequence that encodes the desired protein. Regulatory elements are preferably selected that are operable in the species to which they are to be administered.

Initiation codons and stop codons are preferably included as part of a nucleotide sequence that encodes the CEA and CD40 ligand protein in a genetic vaccine of the present invention. The initiation and termination codons must be in frame with the coding sequence.

Promoters and polyadenylation signals included in a vaccine of the present invention are preferably selected to be functional within the cells of the subject to be immunized.

Examples of promoters useful in the vaccines of the present invention, especially in the production of a genetic vaccine for humans, include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, Cytomegalovirus (CMV) such as the CMV immediate early promoter, Epstein Barr Virus (EBV), Rous Sarcoma Virus (RSV) as well as promoters from human genes such as human actin, human myosin, human hemoglobin, human muscle creatine, and human metalothionein. Other useful promoters include tissue specific promoters such as tumor endothelium-directed promoters, as well as tumor-selective promoters such as CEA promoters, and treatment-responsive promoters such as early growth response promoters.

Examples of polyadenylation signals useful in the vaccines of the present invention, especially in the production of a genetic vaccine for humans, include but are not limited to SV40 polyadenylation signals and LTR polyadenylation signals.

In addition to the regulatory elements required for DNA expression, other elements may also be included in the DNA molecule. Such additional elements include enhancers. Enhancers include the promoters described hereinabove. Preferred enhancers/promoters include, for example, human actin, human myosin, human hemoglobin, human muscle creatine and viral enhancers such as those from CMV, RSV and EBV.

An additional element can be added to the vaccine to serve as a target for cell destruction if it is desirable to be able to eliminate cells receiving the genetic construct for any reason. For example, a herpes thymidine kinase (tk) gene, in an expressible form, can be included in the vaccine. The drug gancyclovir can be administered to the immunized subject, which will cause the selective killing of any cell producing tk. Such means for introducing genetic targets for selective destruction of cells are known and are described in U.S. Pat. No. 5,817,637 to Weiner et al.

Regulatory sequences and codons are generally species dependant. In order to maximize protein production, the regulatory sequences and codons are preferably selected to be effective in the species to be immunized. One having ordinary skill in the art can produce DNA constructs that are functional in a given subject species.

DNA useful in the vaccines of the present invention also includes "naked" DNA as defined in Restifo et al. *Gene Therapy*, 2000, 7:89–92, the pertinent disclosure of which is incorporated by reference. Alternatively, the DNA can be operably incorporated in a carrier or delivery vector. Useful delivery vectors include biodegradable microcapsules, immuno-stimulating complexes (ISCOMs) or liposomes, and genetically engineered attenuated live carriers such as viruses or bacteria.

Examples of suitable attenuated live bacterial carriers/delivery vectors include *Salmonella typhimurium, Salmonella typhi, Listeria monocytogenes, Shigella, Bacillus, Lactobacillus, Bacille Calmette-Guérin* (BCG), *Escherichia coli, Vibrio cholerae, Campylobacter*, and any other suitable bacterial vector, as is known in the art. Preferred bacterial delivery vectors include attenuated *Salmonella typhimurium* and attenuated *Listeria monocytogenes*; particularly preferred is attenuated *Salmonella typhimurium*. Methods of transforming live bacterial vectors with an exogenous DNA construct are well described in the art. See, for example, Joseph Sambrook and David W. Russell, *Molecular Cloning, A Laboratory Manual,* 3rd Ed., Cold Spring Harbor Laboratory Press, Cold Spring Harbor, N.Y. (2001).

Preferred attenuated viral carriers include Herpes viruses, Adenoviruses, Vaccinia virus, and Avipox virus. Methods of transforming a viral vector with an exogenous DNA construct are also well described in the art. See Sambrook and Russell, above.

Liposome carriers are unilamellar or multilamellar vesicles, having a membrane portion formed of lipophilic material and an interior aqueous portion. The aqueous portion is used in the present invention to contain the polynucleotide material to be delivered to the target cell. It is generally preferred that the liposome forming materials have a cationic group, such as a quaternary ammonium group, and one or more lipophilic groups, such as saturated or unsaturated alkyl groups having about 6 to about 30 carbon atoms. One group of suitable materials is described in European Patent Publication No. 0187702, and further discussed in U.S. Pat. No. 6,228,844 to Wolff et al., the pertinent disclosures of which are incorporated by reference. Many other suitable liposome-forming cationic lipid compounds are described in the literature. See, e.g., L. Stamatatos, et al., *Biochemistry* 27:3917–3925 (1988); and H. Eibl, et al., *Biophysical Chemistry* 10:261–271 (1979). Alternatively, a microsphere such as a polylactide-coglycolide biodegradable microsphere may be utilized. A DNA is encapsulated or otherwise complexed with the liposome or microsphere for delivery of the DNA to a tissue, as is known in the art.

The inventive vaccine can also be administered in conjunction with a facilitating agent that improves the uptake of the genetic material of the vaccine by the treated cells. In some preferred embodiments, the DNA can be formulated with or administered in conjunction with a facilitator selected from the group consisting of benzoic acid esters, anilides, amidines, urethans and the hydrochloride salts thereof such as those of the family of local anesthetics, such as disclosed in U.S. Pat. No. 6,248,565 to Williams et al., the pertinent disclosures of which are incorporated herein by reference.

In a method aspect of the present invention, a DNA vaccine can be utilized to provide long term protection against CEA presenting cells such as colon cancer cells, in a vaccinated patient. In one preferred method embodiment a DNA vaccine comprising a plasmid DNA operably encoding both CEA and a CD40 ligand, SEQ ID NO: 1 and SEQ ID NO: 2, respectively (e.g., pCEA-CD40LT), is administered to a mammal in need of protection against CEA presenting cells, in an amount that is sufficient to elicit an immune response against CEA presenting cells.

In another preferred method embodiment of the present invention, tumor growth is inhibited by vaccination of a mammal with the pCEA-CD40LT vaccine of the present invention. In such a method embodiment, an immune response eliciting effective amount of a vaccine comprising a plasmid DNA construct operably encoding both CEA and CD40L, SEQ ID NO: 1 and SEQ ID NO: 2, respectively, is administered to a mammal having a growing tumor comprising CEA presenting cells. The vaccination results in tumor growth arrest and minimizes formation of new tumors by immunizing the mammal against the tumor cells.

In yet another method aspect of the present invention, a mammal is sequentially administered (a) a DNA vaccine comprising a plasmid DNA encoding CEA and a plasmid DNA encoding a CD40 ligand, SEQ ID NO: 1 and SEQ ID NO: 2, respectively, in an amount effective for eliciting an immune response against CEA presenting cells such as colon cancer cells, and (b) an immune response enhancing effective amount of recombinant, humanized KS-1/4 antibody—IL2 fusion protein (huKS-1/4-IL2). Hu KS-1/4-IL2 is described in detail by Gillies et al. *J. Immunol.*, 1998, 160:6195–6203, the relevant disclosure of which is incorporated herein by reference.

IL2 is a complex cytokine produced by activated T cells, which stimulates growth of both B cells and T cells. IL2 activation of T cells also stimulates the production of CD40 ligand on the T cell surface (see generally, Chapter 7 of Charles A. Janeway, Jr. and Paul Travers, *Immunobiology The Immune System in Health and Disease*, Second Edition, Garland Publishing Co., New York, 1996). The role of IL2 targeted to a tumor microenvironment by huKS-114-IL2 fusion protein is to boost anti-tumor T cell responses either by acting as a second costimulatory signal in the activation of CTLs or by further activating pre-activated DCs expressing IL2 receptors. The huKS-1/4-IL2 fusion protein thus enhances the immune responsiveness of the mammal treated with the DNA vaccine so that the immune system more effectively attacks CEA presenting cells, thereby enhancing the effectiveness of the vaccination.

In the method embodiments of the present invention, the vaccines preferably are administered enterally, such as by oral administration, or parenterally, such as by intravenous infusion. In some preferred embodiments, the vaccine is administered intramuscularly, intranasally, intraperitoneally, subcutaneously, intradermally, topically, or orally. Most preferably the vaccine is administered orally, incorporated in an attenuated bacterial delivery vector. Preferably, the vaccines are provided in a pharmaceutically acceptable carrier, such as physiologically saline solution, dextrose solution, and the like, as is well known in the art.

Patients suffering from epithelial cancers, such as cancers of the colon, pancreas, lung and breast, can benefit from immunization by the vaccines of the present invention.

Vaccines of the present invention are preferably formulated with pharmaceutically acceptable carriers and exipients such as water, saline, dextrose, glycerol, ethanol, and the like, and combinations thereof. The vaccines can also contain auxiliary substances such as wetting agents, emulsifying agents, buffers, and the like.

The vaccines of the present invention are preferably administered orally to a mammal, such as a human, as a solution or suspension in a pharmaceutically acceptable carrier, at a DNA concentration in the range of about 10 micrograms per milliliter to about 100 micrograms per milliliter. The appropriate dosage will depend upon the subject to be vaccinated, and can depend upon the capacity of the subject's immune system to express the nucleic acids contained in the vaccine. The exact dosage chosen may also depend, in part, upon the judgment of the medical practitioner administering or requesting administration of the vaccine.

Another embodiment of the present invention is a kit comprising the vaccines of the present invention packaged in suitably sterilized containers such as ampules, bottles, vials, and the like, either in multi-dose or in unit-dosage forms. The containers are preferably hermetically sealed after being filled with a vaccine preparation. Preferably, the vaccines are packaged in a container having a label affixed thereto, which label identifies the vaccine, and bears a notice in a form prescribed by a government regulatory agency such as the United States Food and Drug Administration reflecting approval of the vaccine under appropriate laws, dosage information, and the like. The label preferably contains information about the vaccine that is useful to a health care professional administering the vaccine to a patient. The kit also preferably contains printed informational materials relating to the administration of the vaccine, instructions, indications, and any necessary required warnings.

The kit of the present invention can also contain recombinant antibody fusion protein huKS1/4-IL2 packaged in suitably sterilized containers such as ampules, bottles, vials, and the like, either in multi-dose or in unit-dosage forms. Preferably, the fusion protein is packaged in a container having a label affixed thereto, which label identifies the vaccine, and bears a notice in a form prescribed by a government agency such as the United States Food and Drug Administration reflecting approval of the fusion protein under appropriate laws, dosage information, and the like. The label preferably contains information about the fusion protein that is useful to a health care professional administering the fusion protein to a patient. The printed informational materials present in the kit, also preferably contains information relating to the administration of the fusion protein, instructions, indications, and any necessary required warnings.

In particularly preferred embodiments of the vaccine, the plasmid DNA encoding a CD40 ligand encodes CD40 ligand trimer (CD40LT). It is particularly preferred that the plasmid DNA encoding both CEA and CD40LT is operably incorporated in an attenuated bacterial delivery vector. Preferred bacterial delivery vectors are attenuated *Salmonella typhimurium* and attenuated *Listeria monocytogenes*, most preferably attenuated *Salmonella typhimurium*. Vaccines of the present invention comprising a nucleic acid encoding CD40LT in combination with a DNA encoding CEA can simultaneously stimulate two different immune response systems (i.e. cellular and humoral immunity).

The nucleotide sequences of some members of the carcinoembryonic antigen family are known in the art. The nucleotide sequence encoding a human CEA gene has been disclosed by Schrewe et al., in the EMBL database of the European Bioinformatics Institute, Wellcome Trust Genome Campus, Hinxton, Cambridge CB10 1SD, UK (EMBL accession number is EMBL:HSCEA01), the disclosure of which is incorporated herein by reference (FIG. 7, SEQ ID NO: 1).

Human CD40 ligand (CD40L) is a 154 amino acid protein that plays a central role in regulation of humoral immunity. The DNA sequence encoding human CD40L (also known as CD 154) has been published by Grammar et al., in the EMBL database of the European Bioinformatics Institute, Wellcome Trust Genome Campus, Hinxton, Cambridge CB10 1SD, UK (EMBL accession number is EMBL:HACD40L), the disclosure of which is incorporated herein by reference (FIG. 8, SEQ ID NO: 2). The DNA sequence encoding murine CD40L has been published by Marra et al., in the EMBL database of the European Bioinformatics Institute, Wellcome Trust Genome Campus, Hinxton, Cambridge CB10 1SD, UK (EMBL accession number is EMBL:AI385482), the disclosure of which is incorporated herein by reference (FIG. 9, SEQ ID NO: 3).

Due to the inherent degeneracy of the genetic code, other DNA sequences that encode substantially the same, or a functionally equivalent amino acid sequence to CEA and/or CD40 ligand can be used in the practice of the present invention. Such DNA sequences also include those which are capable of hybridizing to the CEA and/or CD40 ligand sequences.

Altered DNA sequences that can be used in accordance with the present invention include deletions, additions or substitutions of different nucleotide residues resulting in a sequence that encodes the same or a functionally equivalent gene product. The gene product itself may contain deletions, additions or substitutions of amino acid residues within the CEA and/or CD40 ligand sequences, which result in a silent change, thus producing functionally equivalent CEA and/or CD40 ligand proteins. Such amino acid substitutions can be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine, asparagine, glutamine; serine, threonine; phenylalanine, tyrosine.

As used herein, "a functional equivalent" of CD40 ligand refers to a ligand that binds to CD40 or fragments thereof, but not necessarily with the same binding affinity as native CD40 ligand. In like manner, a functional equivalent of CEA refers to a protein that will bind to antisera raised against human CEA, but not necessarily with the same binding affinity as native human CEA.

As used herein, and in the appended claims, the term carcinoembryonic antigen (CEA) includes the natural antigen found in humans and functional equivalents thereof; and the term "CD40 ligand" includes monomers, dimers, and trimers of the natural ligands found in mammals and functional equivalents thereof. Preferably the functional equivalents of the CEA and/or CD40 ligand DNA share at least about 80% homology with the DNA encoding the aforementioned CEA and/or CD40 ligand proteins.

The DNA sequences of the invention can be engineered in order to alter the CEA and/or CD40 ligand coding sequence for a variety of ends including, but not limited to, alterations that modify processing and expression of the gene product. For example, mutations can be introduced using techniques that are well known in the art, e.g. site-directed mutagenesis, to insert new restriction sites, and the like.

The following examples are provided to further illustrate the features and embodiments of the present invention, and are not meant to be limiting.

Materials and Methods

Reagents: T-STIM culture supplement was obtained from BD Biosciences, Bedford, Mass. Fluorescein isothiocyanate (FITC) and R-Phycoerythrin (PE) were obtained from BD Pharmingen, LaJolla Calif. FITC-labeled and PE-labeled antibodies were prepared according to the manufacturer's recommended protocols. All antibodies were obtained from BD Biosciences, Bedford, Mass. Hu KS-1/4-IL2 was prepared as described by Gillies et al., *J. Immunol.*, 1998, 160:6195–6203, the relevant disclosure of which is incorporated herein by reference.

CEA Transgenic Mice: C57B1/6J CEA-transgenic breeder mice were generated by using a 32.6 Kb AatII restriction fragment containing the entire human CEA genomic region (SEQ ID NO: 1) and flanking sequences isolated from a genomic cosmid clone. A mouse cell line [C57B1/6J-TgN (CEAGe) 18; FJP] was established by the method of Clarke et al. *Cancer Res.* 1998, 58:1469, the relevant disclosure of which is incorporated herein by reference. CEA transgenic mice were bred at The Scripps Research Institute's animal care facility. Mice were used between 6 and 8 weeks of age. All animal experiments were performed according to National Institutes of Health *Guide for the Care and Use of Laboratory Animals*.

Tumor Cell Lines and Bacterial Strains: The chemically induced murine colon adenocarcinoma cell line, MC38, was stably transfected with both, CEA (C15-4.3 clone) and the epithelial cell adhesion molecule Ep-CAM/KSA as described in Gilles et al. *J. Immunol.*, 1998, 160:6195. The attenuated *Salmonella typhimurium* AroA Strain SL 7207 was kindly provided by Dr. B. A. D. Stocker (Stanford University, Stanford, Calif.). Chemically competent *E. coli* were purchased from Invitrogen (Carlsbad, Calif.) and routinely grown at 37° C. in LB broth or on agar plates (VWR), supplemented when necessary with 75 µg/ml ampicillin as is known in the art.

Construction of Expression Plasmids: Several distinct forms of expression plasmids were generated to target CD40LT and CEA molecules to DCs or T cells, respectively. The plasmids used for immunization were constructed from pcDNA3.1/zeo(+) (Invitrogen). The pER-CEA control plasmid targeted to and retained in the endoplasmic reticulum (ER), and the pW-CEA plasmid targeted to the cell surface, have been described previously by Xiang et al. *Clin. Cancer Res.*, 2001, 3:8565, the relevant disclosure of which is incorporated herein by reference. The plasmid encoding the CD40LT gene (pCD40LT) contained a modified 33 amino acid leucine zipper motif in order to facilitate the formation of trimeric CD40L that was fused to the C-terminus of the IL7 leader sequence to direct protein expression to the cell surface or induce its secretion outside the cells, as described by Fanslow et al. *Semin. Immunol.*, 1994, 6:267, the relevant disclosure of which is incorporated herein by reference. Detection of CD40LT by Western blotting was facilitated by incorporating a short antigenic sequence, Flag, detectable by specific monoclonal antibodies. The plasmid pCEA-CD40LT contained the entire CEA extracellular domain fused to the C-terminus of murine CD40L, thus generating a dual-function chimeric construct.

Oral Immunization, Tumor Cell Challenge and Antibody-IL2 Fusion Protein Boosts: CEA-transgenic C57BL/6J mice were divided into seven experimental groups (n=8). Mice were immunized three times at two-week intervals by oral gavage with 100 µl PBS containing $1 \times 10^8$ transformed, attenuated *S. typhimurium* harboring either empty vector (pcDNA3.1), individual expression vectors pER-CEA (control vaccine), pW-CEA (control vaccine), pCD40LT (control vaccine), pCEA-CD40LT (inventive vaccine), or the inventive vaccine followed by boosts with huKS1/4-1L2. Other control experiments included oral gavage with PBS, and recombinant antibody fusion protein huKS1/4-IL2 boosts without immunization by DNA vaccine, and a group of mice vaccinated only with irradiated MC38 cells. All mice were challenged subcutaneously in the right flank with a lethal dose of $2.5 \times 10^5$ MC38-CEA-KSA cells two weeks after the last immunization. Mice were examined daily until the tumor became palpable, after which its diameter was measured in two dimensions with a microcaliper every other day.

Construction of the huKS1/4-IL2 fusion protein has been described previously by Gillies et al. *J. Immunol.*, 1998, 160:6195–6203, the relevant disclosure of which is incorporated herein by reference. C57BL/6J mice transgenic for CEA that were immunized by oral gavage with the transformed, attenuated *S. typhimurium* vaccine described as above, received 5 µg boosts of huKS1/4-IL2 fusion protein for five consecutive days starting one day after tumor cell challenge.

Cytotoxicity Assay: Cytotoxicity was measured by a standard $^{51}$Cr-release assay according to the method of Xiang et al. *Cancer Res.*, 1997, 57:4948, the relevant disclosure of which is incorporated herein by reference. Splenocytes isolated from CEA-transgenic mice, one week after tumor cell challenge, were subsequently cultured for three days at 37° C. in complete T-STIM culture medium (Beckton Dickinson, Bedford, Mass.). MC38-CEA-KSA target cells (3×10$^6$), labeled with 0.5 mCi of $^{51}$Cr were incubated with effector cells at various Effector:Target cell (E:T) ratios at 37° C. for four hours.

Transfection and Immunoblot Assessment of Protein Expression: Lipofectamine was used for transient transfection of COS-7 cells according to the manufacturer's instructions (Invitrogen), seeding COS-7 cells at 2.5×10$^5$ cells per well in a six-well plate and adding 24 hours later, 1 μg of DNA with 5 μl lipofectamine in serum-free medium. Immunoblots were performed with equal quantities of protein (15 μl/lane), separated by SDS-PAGE under reducing and non-reducing conditions alongside a control lysate and electroblotted onto a nitrocellulose membrane as described previously (Xiang et al. *Cancer Res.*, 1997, 57:4948). After staining with mouse anti-human CEA mAb (ICN, Aurora, Ohio) or anti-FLAG M2 mAb (Sigma, St. Louis, Mo.), followed by anti-mouse IgG-HRP, the blot was developed with ECL Western blotting detection reagents (Amersham Pharmacia Biotech, Piscataway, N.J.) and XOMAT-5 film (Eastman Kodak Company, Rochester, N.Y.).

Flow Cytometry Analysis: Activation markers of T cells and expression of costimulatory molecules on CD11c and MHC class II antigen-positive DCs were determined by two-color flow cytometry analysis with a Becton Dickinson FACScan. T cell activation was determined by staining of freshly isolated splenocytes from successfully vaccinated mice with anti-CD8 FITC (53-6.7), in combination with PE-conjugated anti-CD25 (H129.19), LFA-1(2D7), CD28 (37.51) and CD69 (H1.2F3) antibodies. Activation of costimulatory molecules on APCs was measured with FITC-labeled anti-CD 11c (HL-3), in combination with PE-conjugated anti-B7.1 (16-10A1), B7.2 (GL1) or ICAM-1, and biotinylated anti-IA$^b$ (KH74) antibodies followed by streptavidinallophycocyanin. All cytometric flow experiments were performed in the presence of 0.1 μg/ml propidium iodide to exclude dead cells. All reagents were obtained from BD Pharmingen (LaJolla, Calif.).

Cytokine Induction Assay: Splenocytes were harvested from all experimental groups of mice one week after subcutaneous lethal tumor cell challenge with 2.5×10$^5$ MC38-CEA-KSA cells. Lymphocytes were isolated on Ficoll-Hypaque (BioWhittaker, Walkersville, Md.) and cultured 24 hours in complete T cell medium with 1×10$^5$ irradiated (15,000 rad) MC38-CEA-KSA cells. Supernatants were collected and stored at −70° C. until use. Cytokines were analyzed for either IFN-γ or IL12 with commercially available cytokine detection kits using a solid-phase sandwich ELISA (R&D Systems, Minneapolis, Minn.).

EXAMPLE 1

Protein Expression of CEA and CD40LT

Protein expression of plasmids pCD40LT, pCEA-CD40LT and pW-CEA were analyzed by transfection into COS-7 cells. Western blotting indicated that all constructs produced proteins of the expected molecular mass (35 kDa, 215 kDa, and 180 kDa, respectively) as shown by SDS/PAGE analyses of lysates from transfected cells, analyzed under reducing conditions (FIGS. 1A and 1B). A plasmid encoding pCD40LT expressed proteins in the cell lysate indicative of monomeric, dimeric and trimeric CD40L, under non-reducing conditions (FIG. 1B). CD40L protein was also detected in supernatants of transfected cells under reducing conditions (FIG. 1A).

EXAMPLE 2

Figure 2:
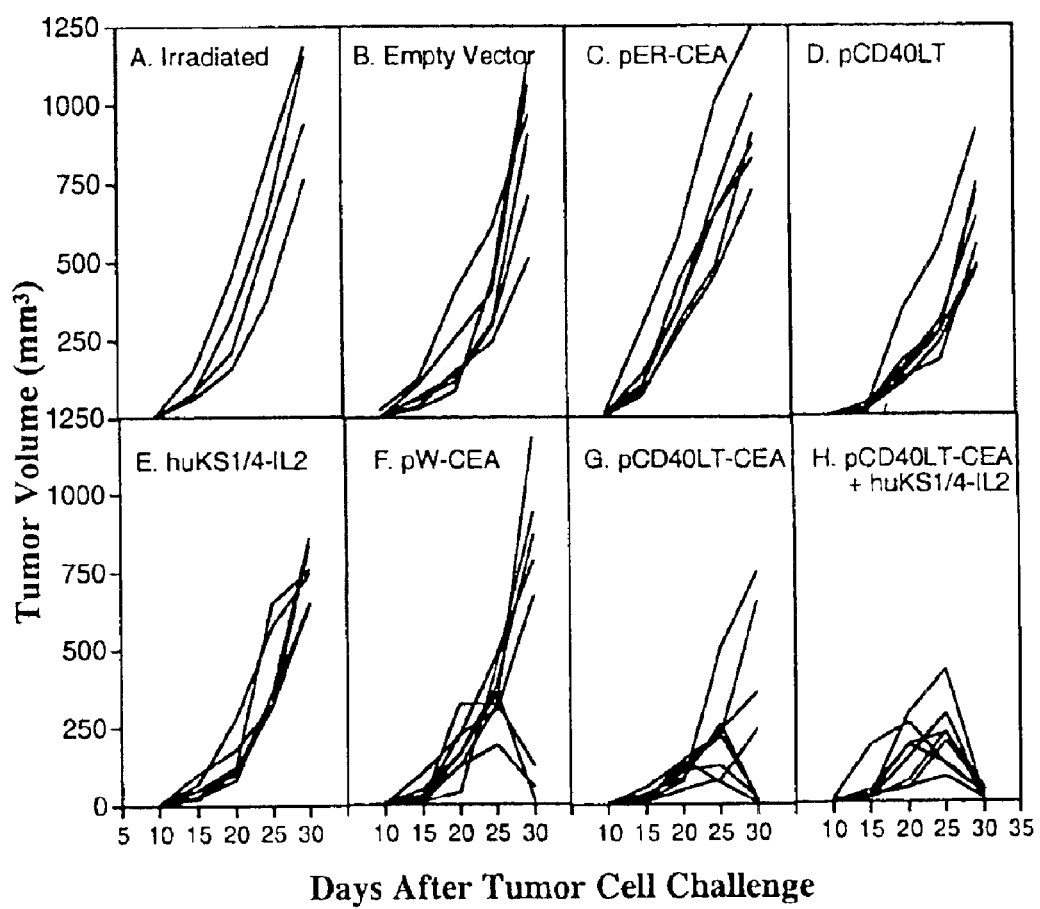
FIG. 2 graphically depicts inhibition of tumor growth in mice vaccinated with the pCEA-CD40LT DNA vaccine of the present invention.

Induction of Tumor Protective Immunity by a Dual-Function Vaccine Encoding both CD40LT and CEA Molecules A number of experiments were performed, including several controls, which indicated that the dual-function DNA vaccine (pCEA-CD40LT) targets CD40LT and CEA to DCs and T cells, respectively. The results are graphically depicted in FIG. 2. In FIG. 2, the tumor growth of each individual mouse is depicted by a solid line. Thus, C57B1/6J mice transgenic for CEA were immunized on days 0 and 7 each by subcutaneous injections of 2.5×10$^5$ irradiated (15,000 rad) MC38 murine colon carcinoma cells. Challenge of these controls two weeks later with a lethal subcutaneous dose of MC38-CEA-KSA cells resulted in rapidly developing tumors in all mice indicating that MC38-CEA-KSA cells were not immunogenic per se (FIG. 2A). This was also found to be the case in three other key control experiments: Mice (n=6) vaccinated three times at two week intervals by oral gavage with 1×10$^8$ attenuated *S. typhimurium* carrying either the empty vector, the pER-CEA plasmid exclusively targeted to and retained in ER, or the pCD40LT construct alone, all uniformly failed to elicit a protective immune response against a lethal subcutaneous tumor cell challenge and revealed rapid and uniform tumor growth (FIGS. 2B, 2C, and 2D). In contrast, a group of mice treated by the same vaccination protocol, but receiving the DNA vaccine containing the pW-CEA vector, revealed a substantial decrease in tumor volume, with 3 of 8 animals completely rejecting the tumor cell challenge (FIG. 2F). In mice vaccinated with the inventive pCEA-CD40LT vaccine, 4 of 8 animals completely rejected the tumor cell challenge. In this case, the remaining mice showed a dramatic suppression of tumor growth when compared to controls (P<0.001) (FIG. 2G).

EXAMPLE 3

Vaccination Efficacy is Amplified by Boosts and Antibody-IL2 Fusion Protein

Boosts with small, non-curative doses of huKS1/4-IL2 fusion protein targeted to the tumor microenvironment markedly increased the efficacy of the inventive DNA vaccine. In fact, vaccination of CEA-transgenic mice by the same protocol described for the pCEA-CD40LT vaccine group, followed by intravenous injections of 5 μg huKS1/4-IL2 one day after tumor cell challenge for five consecutive days, resulted in the complete rejection of the tumor cell challenge in 8/8 experimental animals (FIG. 2H). An important control experiment indicated that the injection of 5×5 μg of huKS1/4-IL2 fusion protein per se had essentially no effect on tumor growth, when administered to naive mice that only had received the tumor challenge without prior immunization by the inventive DNA vaccine (FIG. 2E). The IL2 fusion protein boost was specific, since boosting with a non-specific fusion protein hu14.18-IL2 directed against ganglioside GD2 not expressed by M38 colon carcinoma cells, was quite ineffective.

EXAMPLE 4

Figure 3:
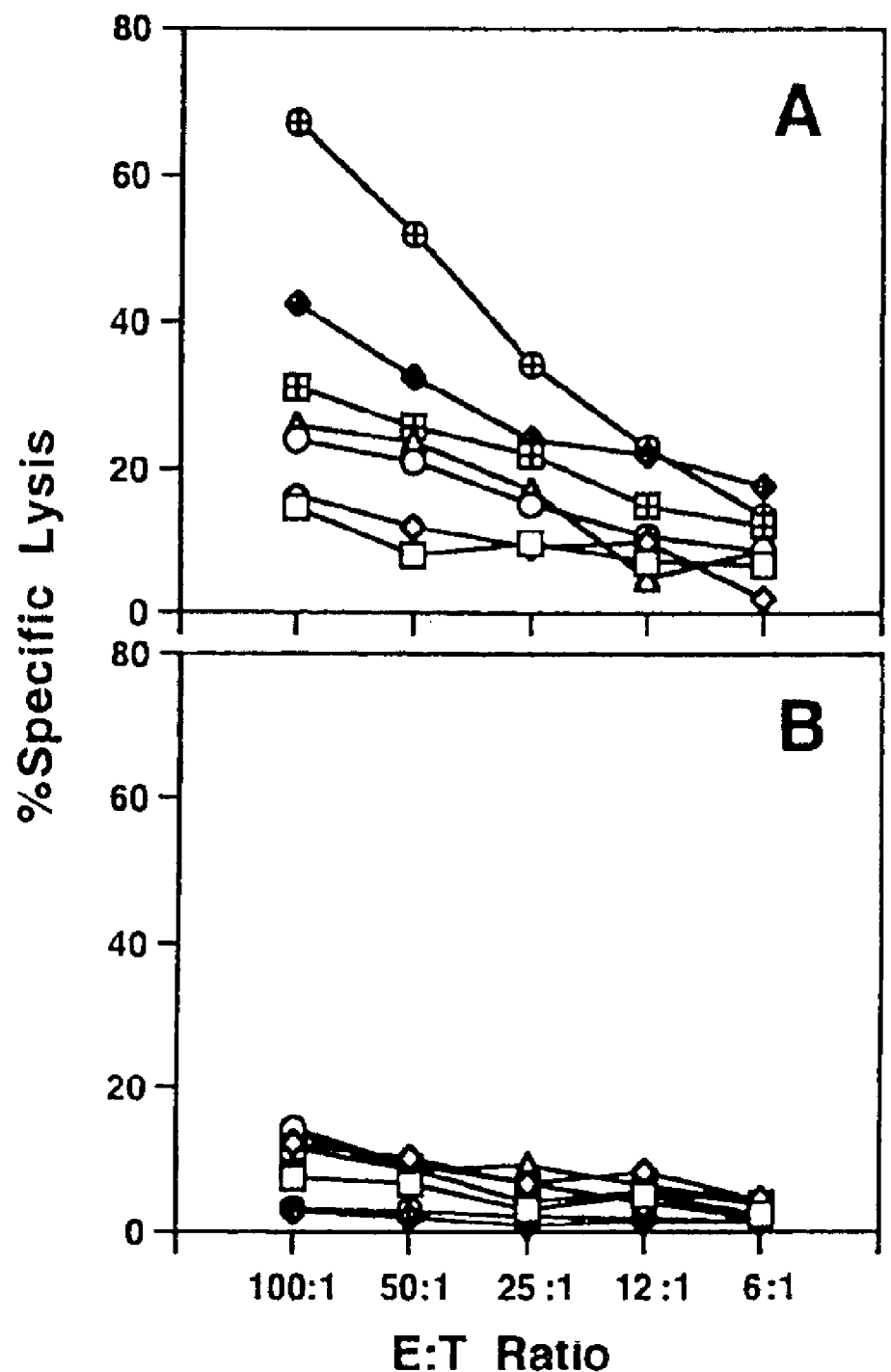
FIG. 3 graphically depicts the ability of splenocytes from mice vaccinated with the DNA vaccine of the present invention to kill MC-38-CEA-KSA tumor cells.

Antigen-Specific CTL Responses are Increased by the Inventive pCEA-CD40LT Dual Function Vaccine The application of the pCEA-CD40LT vaccine of the present invention induced strong cytotoxic CD8$^+$ T cell priming, either with or without huKS1/4-IL2 fusion protein boosts, as demonstrated in CEA-transgenic mice immunized with each of the individual plasmids (FIG. 3). In FIG. 3, data for untreated tumor-bearing mice are indicated by (□), mice treated only with fusion protein are indicated by (◇), mice immunized with plasmid pER-CEA are indicated by (○), mice immunized with pCEA-CD40LT are indicated by (Δ), mice immunized with pW-CEA are indicated by (⊞), mice immunized with pCEA-CD40LT are indicated by (◆), and mice immunized with pCEA-CD40LT and huKS1/4-IL2 are indicated by (⊕). CTLs of mice that received vaccinations with pCEA-CD40LT vaccine plus boosts with the antibody-IL2 fusion protein proved to be most effective, inducing up to 70% lysis as compared to 45% lysis by such cells obtained from mice immunized with the same vaccine but without the fusion protein boost (FIG. 3A). In contrast, only background lysis was observed with splenocytes obtained from control animals. Tumor cell lysis was specific since the use of non-specific B16 melanoma cells lacking CEA expression as targets resulted in a complete lack of cytolysis. Importantly, the data depicted in FIG. 3B clearly demonstrate that the cytolytic response elicited by splenocytes from mice immunized against MC38-CEA-KSA tumor target cells was MHC class I antigen-restricted, since the presence of 50 μg/ml antibodies directed against H2-K$^b$/H2-D$^b$ MHC class I antigens completely inhibited cytotoxic activities. This inhibitory effect was specific, since the presence of non-specific anti-H-2K$^d$ and H-2D$^d$ antibodies did not inhibit cytolysis.

EXAMPLE 5

Figure 4:
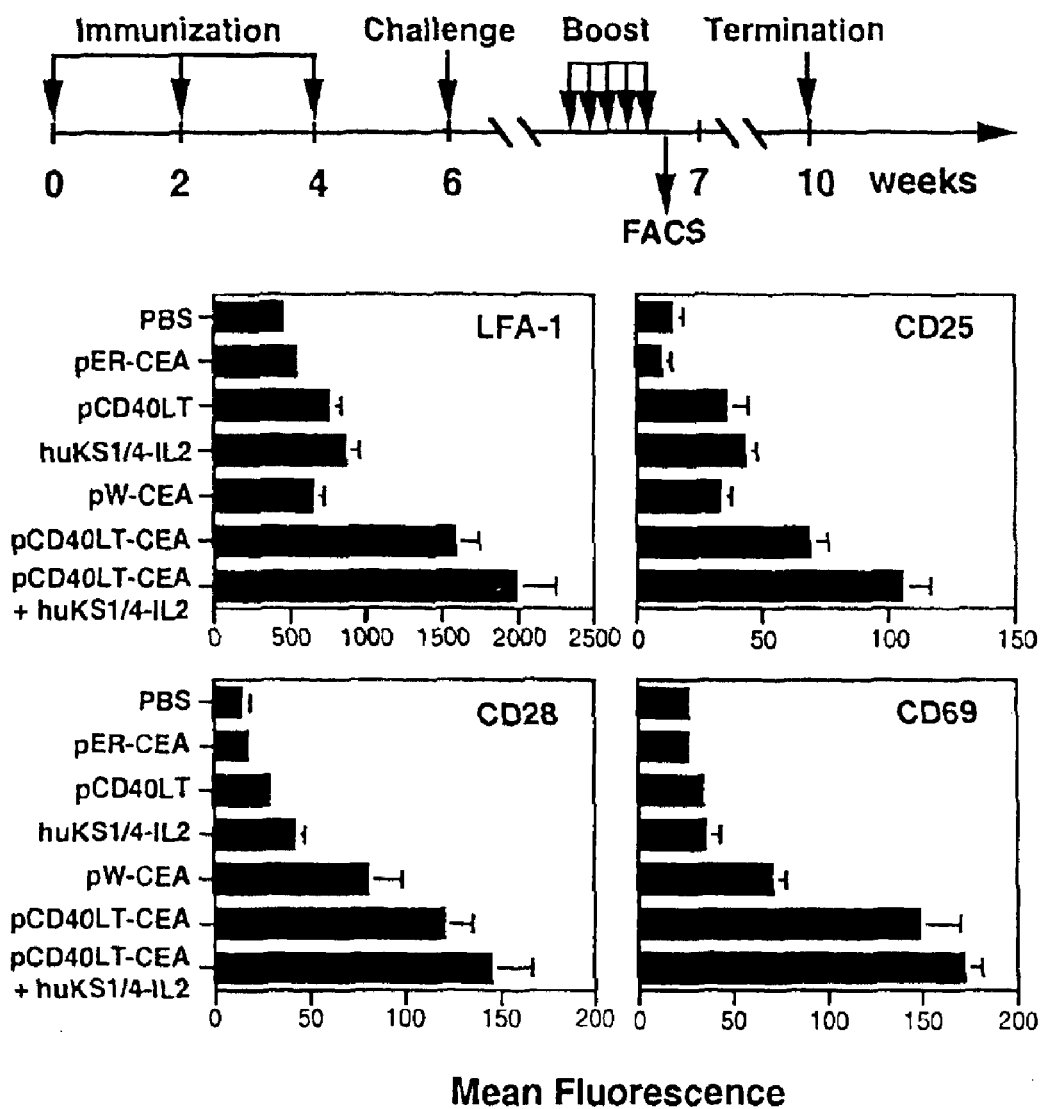
FIG. 4 graphically depicts upregulated expression of T cell activation molecules in mice vaccinated with the pCEA-CD40LT DNA vaccine of the present invention, and enhanced upregulation when the vaccinated mice are further treated with huKS1/4-IL2 fusion protein boosts.

Upregulation of CTL Activity Markers by the Dual-Function DNA Vaccine of the Invention is Enhanced by Boosts with Antibody-IL2 Fusion Protein The interaction between CD40LT on activated T helper cells with its CD40 target on DCs is important for achieving optimal antigen-specific T cell responses. A correlation was observed between the ability of the dual function DNA vaccine to enhance T cell-dependent immune responses and the increase in expression of T cell activation markers. This was evident from increases in expression of CD25, the high affinity IL2 receptor α chain, CD69, an early T cell activation antigen, and the lymphocyte function-associated antigen, LFA-1, important for the initial interaction between T cells and DCs via the intercellular cell adhesion molecule, ICAM-1 (FIG. 4). Importantly, these upregulated T cell activation markers also included CD28, a member of the Ig superfamily expressed on T cells which serves as the receptor for the costimulatory B7.1 and B7.2 molecules of DCs whose ligation with CD28, in turn, will costimulate growth of naive T cells (FIG. 4). Surprisingly, boosts with huKS1/4-IL2 fusion proteins 24 hours after tumor cell challenge further elevated expression of these same markers by 20% to 35%.

EXAMPLE 6

Figure 5:
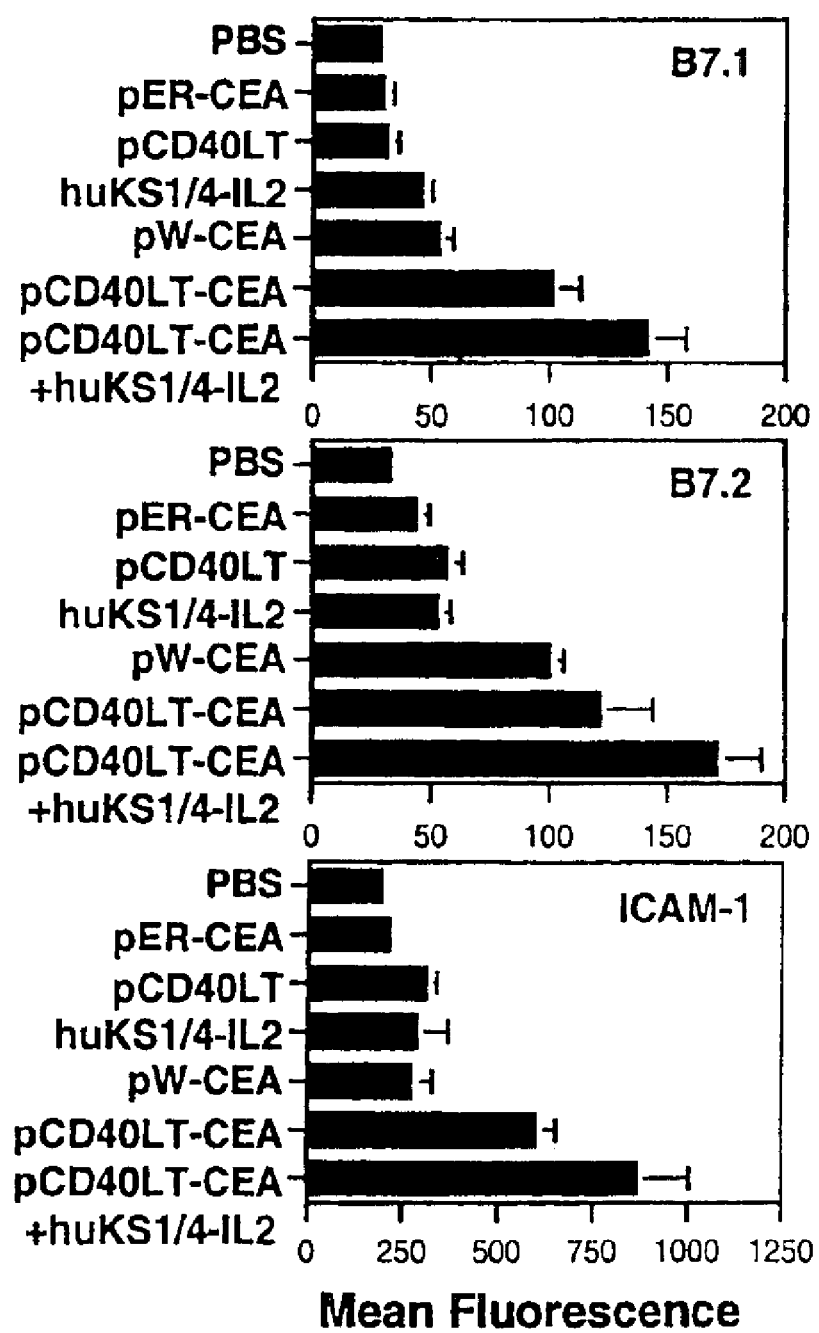
FIG. 5 graphically depicts the enhanced expression of costimulatory molecules in mice vaccinated with the pCEA-CD40LT DNA vaccine of the present invention when the vaccinated mice are further treated with huKS1/4-IL2 fusion protein boosts.

Increased Expression of Costimulatory Molecules by Immunization with pCEA-CD40LT Vaccines and Boosts by Antibody-IL2 Fusion Protein T cell activation is dependent on upregulated expression of costimulatory molecules B7.1 and B7.2 on DCs to achieve optimal ligation with CD28 expressed on T cells. Equally important is the upregulation of ICAM-1, which binds the T cell integrin LFA-1. Flow cytometry analyses of splenocytes obtained from CEA-transgenic mice, successfully immunized with the inventive DNA vaccine and boosted with antibody-IL2 fusion protein, clearly indicated that this upregulation was accomplished very effectively, since the expression of B7.1, B7.2 and ICAM-1 was upregulated one to two-fold over that of controls (FIG. 5). Boosts with antibody-IL2 fusion protein resulted in an additional 20% to 40% increase in expression of both costimulatory and adhesion molecules (FIG. 5). These data provide evidence that vaccination with pCEA-CD40LT molecules induce and enhance the expression of costimulatory molecules on CD11c$^+$ and MHC class II antigen-positive DCs, demonstrating that the capability of these APCs for tumor specific antigen processing and presentation was significantly increased.

Figure 6:
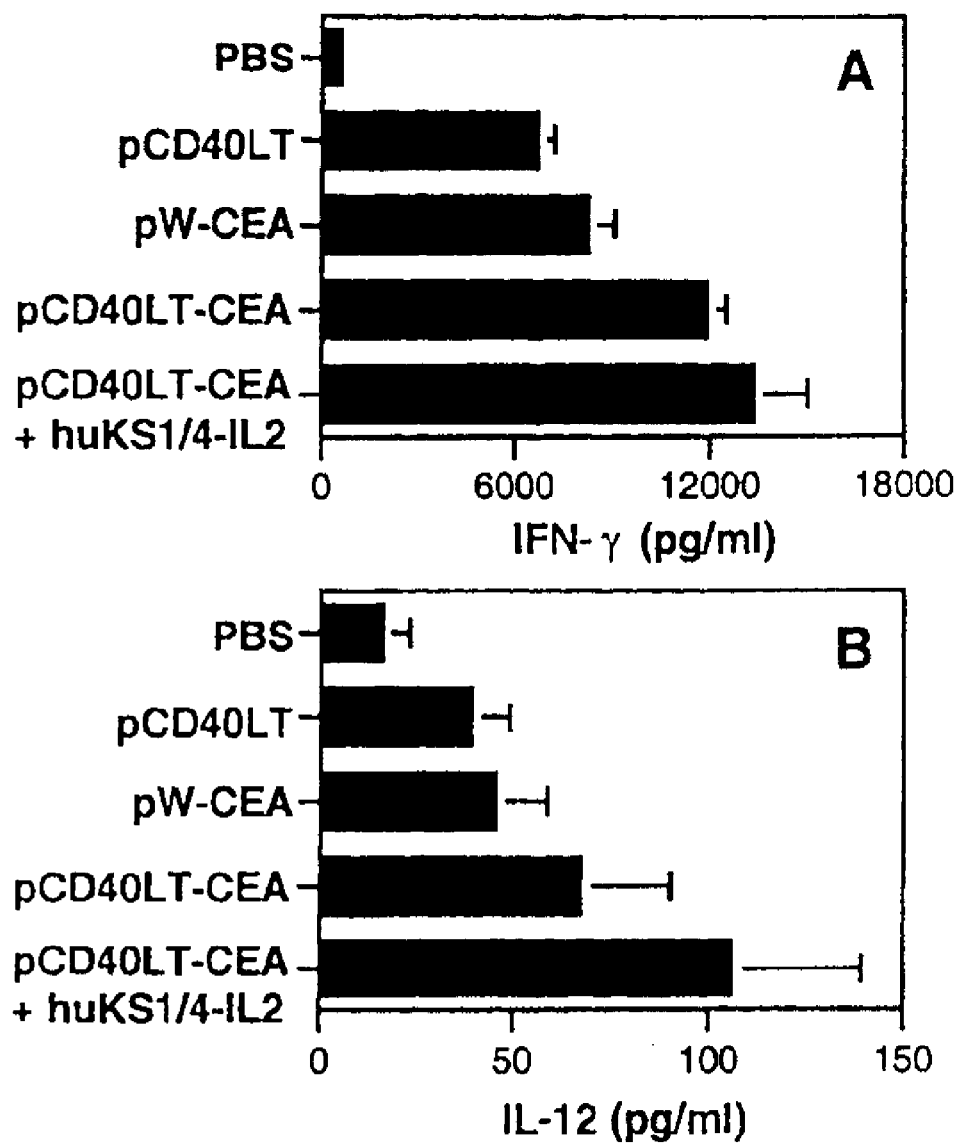
FIG. 6 graphically depicts the induction of pro-inflammatory cytokines in mice vaccinated with a pCEA-CD40LT DNA vaccine of the present invention, and the enhancement of that induction when the vaccinated mice are treated with huKS1/4-IL2 fusion protein boosts.

EXAMPLE 7 pCEA-CD40LT Vaccination Enhances Production of Cytokines Boosted Further by Antibody-IL2 Fusion Protein The pCEA-CD40LT vaccine enhanced the release of pro-inflammatory cytokines, IFN-γ and IL2 from T cells, as indicated by a solid-phase sandwich ELISA measuring their production in supernatants of various splenocyte preparations 24 hours after being plated in the presence of irradiated (15,000 rad) MC38-CEA-KSA tumor cells. Only background levels of IFN-γ and IL12 were detected when analyzing supernatants of splenocytes obtained from PBS treated CEA-transgenic control mice after challenge with MC38-CEA-KSA cells. However, if mice received the pCEA-CD40LT DNA vaccine, the production of IFN-γ and IL12 increased by 75% and 50%, respectively, over those levels observed in mice vaccinated with either pCD40LT or pW-CEA alone (FIG. 6). Production of IFN-γ was further augmented by 25% after boosts with huKS1/4-IL2 fusion protein, while that of IL12 increased 3-fold over control values and 100% over that observed after vaccination, but without the huKS1/4-IL2 boost (FIG. 6). These data demonstrate that DNA immunization with the vaccine of the present invention coupled with boosts of antibody-IL2 fusion protein decisively increased T cell activation in secondary lymphoid tissues.

Discussion

CEA-transgenic mice, which produce the human tumor self-antigen CEA, provide a useful model organism for the development and evaluation human anti-tumor treatments. The dual functional oral DNA vaccine of the present invention has surprisingly broken peripheral T cell tolerance against CEA, in CEA-transgenic mice. Importantly, a CD8$^+$ T cell-mediated rejection of a lethal challenge of murine colon carcinoma cells occurred that was completely effective in 100% of experimental mice in a prophylactic setting. The previously reported tumor-protective immunity achieved with a CEA-based DNA vaccine in CEA-transgenic mice was never completely effective in all experimental animals. Surprisingly, successful tumor-protective immunity was achieved in CEA-transgenic mice treated with the vaccine of the present invention, especially when utilized in conjunction with booster injections of the recombinant antibody fusion protein huKS1/4-IL2.

The vaccines of the present invention upregulated the expression of several receptor/ligand pairs known to critically impact effective activation of T cells following their interaction with DCs that present them with MHC:peptide complexes. The inventive vaccine upregulated CD40/CD40LT, LFA-1/ICAM-1, CD28/B7.1 and B7.2 and CD25/

IL2, and increased the secretion of pro-inflammatory cytokines IFN-γ and IL12. A marked activation of T cells and CD11c+ dendritic-like cells was indicated by the decisive upregulation in expression of T cell integrins LFA-1 and ICAM-1, which are known to synergize in the binding of lymphocytes to APCs.

The transient binding of naive T cells to APCs is important in providing time for these cells to sample large numbers of MHC molecules on the surface of each APC for the presence of specific peptides. Through this mechanism the chance of a naive T cell recognizing its specific MHC:peptide ligand is increased followed by signaling through the TCR and induction of a conformational change in LFA-1. This, in turn greatly enhances LFA-1's affinity for ICAM-1 and stabilizes the association between the antigen-specific T cell and the APC.

The marked increase in expression of CD28 on T cells in as well as the costimulatory molecules B7.1 and B7.2 on DCs, following vaccination with the inventive vaccine and tumor cell challenge, is particularly significant since it provides the two signals required for activation of naive T cells. One signal, indicating antigen recognition being transmitted to T cells after binding of the MHC:peptide complex to the TCR, and the other signal, ligation of CD28 with B7.1 and B7.2, initiating T cell responses and production of armed effector T cells. A clear indication of T cell activation in secondary lymphoid tissues was provided by marked increases in expression of CD25, the high affinity IL2 receptor α-chain and CD69, an early T cell activation antigen.

The significant elevation in the production of pro-inflammatory cytokines IFN-γ and IL12 by T cells induced by the dual-function DNA vaccine of the invention suggests that a third signal may act directly on T cells. This "danger signal", was reported to be required for $T_H1$ differentiation leading to clonal expansion of T cells. In fact, whenever T cell help is required to generate an effective CD8+ T cell response against a tumor-self antigen like CEA, triggering of DCs is necessary prior to their encounter with an antigen-specific CD8+ T cell. This effect is mediated by ligation of CD40 on the surface of APCs with CD40L expressed on activated CD4+ T cells.

CD40LT expressed by the inventive DNA vaccine can act as a surrogate for activated CD4+ T cells, leading to maturation of DCs as indicated by their decisive upregulation of B7.1 and B7.2 costimulatory molecules. The inventive orally administered dual-function DNA vaccine containing genes encoding for both CEA and a CD40 ligand induces a highly efficient tumor-protective immunity against human CEA tumor self-antigen.

Numerous variations and modifications of the embodiments described above may be effected without departing from the spirit and scope of the novel features of the invention. It is to be understood that no limitations with respect to the specific embodiments illustrated herein are intended or should be inferred. It is, of course, intended to cover by the appended claims all such modifications as fall within the scope of the claims.

We claim:

1. A DNA composition effective for eliciting an immune response against cells that present carcinoembryonic antigen (CEA) comprising:
   (a) a first plasmid DNA operably encoding the CEA; and
   (b) a second plasmid DNA operably encoding a CD40 ligand; together with a pharmaceutically acceptable carrier; wherein both plasmid DNAs are operably incorporated in an attenuated bacterial delivery vector selected from the group consisting of *Salmonella typhimurium* and *Listeria monocytogenes*.

2. The DNA composition of claim 1 wherein both plasmid DNAs are operably incorporated in an attenuated *Salmonella typhimurium* delivery vector.

3. The DNA composition of claim 1 wherein the CD40 ligand is CD40LT.

4. A method of inducing an immune response in a mammal against cancer cells that present carcinoembryonic antigen (CEA) which comprises the step of administering to the mammal an immune response eliciting amount of a DNA composition comprising a first plasmid DNA operably encoding the CEA, and a second plasmid DNA operably encoding a CD40 ligand, in an amount sufficient to elicit an immune response against cells that present the CEA; wherein both plasmid DNAs are operably incorporated in an attenuated bacterial delivery vector selected from the group consisting of *Salmonella typhimurium* and *Listeria monocytogenes*.

5. The method of claim 4 wherein the mammal is a human.

6. The method of claim 4 wherein the CD40 ligand is CD40LT.

7. The method of claim 4 wherein the cells presenting a carcinoembryonic antigen are colon cancer cells.

8. The method of claim 4 wherein the composition is administered orally.

9. A DNA Composition effective for eliciting an immune response against cells that present carcinoembryonic antigen (CEA) comprising:
   (a) a first plasmid DNA operably encoding the CEA; and
   (b) a second plasmid DNA operably encoding a CD40 ligand; together with a pharmaceutically acceptable carrier;
   wherein both plasmid DNAs are operably incorporated in an attenuated bacterial delivery vector.

10. The DNA Composition of claim 9 wherein the CD40 ligand is CD40LT.

11. A method of immunizing a mammal against cancer cells that present carcinoembryonic antigen (CEA) which comprises the step of administering to the mammal an effective immune response eliciting amount of a DNA Composition of claim 9.

12. The method of claim 11 wherein the mammal is a human.

13. The method of claim 11 wherein the second plasmid DNA encodes CD40LT.

14. The method of claim 11 wherein the cells presenting a carcinoembryonic antigen are colon cancer cells.

15. The method of claim 11 wherein the Composition is administered orally.

* * * * *

SEQUENCE LISTING

<160> NUMBER OF SEQ ID NOS: 3

<210> SEQ ID NO 1
<211> LENGTH: 3281
<212> TYPE: DNA
<213> ORGANISM: human

<400> SEQUENCE: 1

```
gagctcctca cacggactct gtcagctcct ccctgcagcc tatcggccgc ccacctgagg      60
cttgtcggcc gcccacttga ggcctgtcgg ctgccctctg caggcagctc ctgtccccta     120
caccccctcc ttccccgggc tcagctgaaa gggcgtctcc cagggcagct ccctgtgatc     180
tccaggacag ctcagtctct cacaggctcc gacgccccct atgctgtcac ctcacagccc     240
tgtcattacc attaactcct cagtcccatg aagttcactg agcgcctgtc tcccggttac     300
aggaaaactc tgtgacaggg accacgtctg tcctgctctc tgtggaatcc cagggcccag     360
ccagtgcctg acacggaaca gatgctccat aaatactggt taaatgtgtg ggagatctct     420 aaaagaaac atatccacctc cgtgtggccc ccagcagtca gagtctgttc catgtggaca     480 cagggcact ggcaccagca tgggaggagg ccagcaagtg cccgcggctg ccccaggaat     540
gaggcctcaa cccccagagc ttcagaaggg aggacagagg cctgcaggga atagatcctc     600
cggcctgacc ctgcagccta atcctgagtt cagggtcagc tcacaccacg tcgacctgg     660 tcagcatccc tagggcagtt ccagacaagg ccggaggtct cctcttgccc tccaggggt     720 gacattgcac acagacatca ctcaggaaac ggattcccct ggacaggaac ctggctttgc     780
taaggaagtg gaggtggagc ctggtttcca tcccttgctc caacagaccc ttctgatctc     840
```

-continued

```
tcccacatac ctgctctgtt cctttctggg tcctctgagg acctgttctg ccagggtcc     900
ctgtgcaact ccagactccc tcctggtacc accatgggga aggtggggtg atcacaggac    960
agtcagcctc gcagagacag agaccaccca ggactgtcag ggagaacatg acaggccct    1020
gagccgcagc tcagccaaca gacacggaga gggagggtcc ccctggagcc ttccccaagg   1080
acagcagagc ccagagtcac ccacctccct ccaccacagt cctctctttc caggacacac   1140
aagacacctc ccctccaca tgcaggatct ggggactcct gagacctctg gcctgggtc     1200
tccatccctg ggtcagtggc ggggttggtg gtactggaga cagagggctg gtccctcccc   1260
agccaccacc cagtgagcct ttttctagcc cccagagcca cctctgtcac cttcctgttg   1320
ggcatcatcc caccttccca gagccctgga gagcatgggg agacccggga cctgctgggt   1380
ttctctgtca caaaggaaaa taatccccct ggtgtgacag acccaaggac agaacacagc   1440
agaggtcagc actggggaaa gacaggttgt ccacagggga tgggggtcca tccaccttgc   1500
cgaaagatt tgtctgagga actgaaaata aagggaaaa aagaggaggg acaaaagagg     1560
cagaaatgag aggggagggg acagaggaca cctgaataaa gaccacaccc atgacccacg   1620
tgatgctgag aagtactcct gccctaggaa gagactcagg gcagagggag gaaggacagc   1680
agaccagaca gtcacagcag ccttgacaaa acgttcctgg aactcaagct cttctccaca   1740
gaggaggaca gagcagacag cagagaccat ggagtctccc tcggccctc cccacagatg    1800
gtgcatcccc tggcagaggc tcctgctcac aggtgaaggg aggacaaccc ctgggagagg   1860
gtgggaggag ggagcacaga gactggctgg ggtctcctgg gtaggacagg gctgtgagac   1920
ggacagaggg ctcctgttgg agcctgaata gggaagagga catcagagag ggacaggagt   1980
cacaccagaa aaatcaaatt gaactggaat tggaaagggg caggaaaacc tcaagagttc   2040
tattttccta gttaattgtc actggccact acgttttaa aaatcataat aactgcatca    2100
gatgacactt taaataaaaa cataaccagg gcatgaaaca ctgtcctcat ccgcctaccg   2160
cggacattgg aaaataagcc ccaggctgtg gagggccctg ggaaccctca tgaactcatc   2220
cacaggaatc tgcagcctgt cccaggcact gggtgcaacc aagatcacac aaatccctgc   2280
cctcatgaag ctcatgctct catggggagg aagacagaca tacaaagaga tctagaatgt   2340
gaggtcaggt gttgacaaga gcctggaggg aatagagcag ggaaaggtca gaaaggaag    2400
acccaaggtc tctagaggag gtgtcaggga agggatctcc caagaatgcc ctgatgtgag   2460
caggacctga aggcaatggg gagggagccg tgaagacccc tggaaaagca gattccacac   2520
agggaaatgc caaggtcgga ggtgctaagg aaataggaga cacactgctg accttgacct   2580
agtaggacac acacacacac acacacacac actcactcac tccagggctg ggggatgaag   2640
agacctgctc aggacccagg accccatttt tccaccctaa tgcataggtc ccaatattga   2700
ccgatgctct ctgctctctc ctagcctcac ttctaacctt ctggaacccg cccaccactg   2760
ccaagctcac tattgaatcc acgccgttca atgtcgcaga ggggaaggag gtgcttctac   2820
ttgtccacaa tctgccccag catctttttg gctacagctg gtacaaaggt gaaagagtgg   2880
atggcaaccg tcaaattata ggatatgtaa taggaactca acaagctacc cagggcccg    2940
catacagtgg tcgagagata atataccccca atgcatccct gctgatccag aacatcatcc   3000
agaatgcac aggattctac accctacacg tcataaagtc agatcttgtg aatgaagaag    3060
caactggcca gttccgggta taccgtgagt gattccccca tgacctctgg gtgttggggg   3120
tcagttctac ttcccacaca caggattatc aggcctgggc tgtgctgtgg cccctctgc    3180
attacgaacc atgttagggt ttgggcattt agtgcaggat acacacagaa gagacaaact   3240
```

-continued tcaacagatc agaattcctt tccggcatcc agaccctgca g                3281

<210> SEQ ID NO 2
<211> LENGTH: 839
<212> TYPE: DNA
<213> ORGANISM: human

<400> SEQUENCE: 2

| | | | | | |
|---|---|---|---|---|---|
| ccatttcaac | tttaacacag | catgatcgaa | acatacaacc | aaacttctcc | ccgatctgcg | 60 |
| gccactggac | tgcccatcag | catgaaaatt | tttatgtatt | tacttactgt | ttttcttatc | 120 |
| acccagatga | ttgggtcagc | acttttttgct | gtgtatcttc | atagaaggtt | ggacaagata | 180 |
| gaagatgaaa | ggaatcttca | tgaagatttt | gtattcatga | aaacgataca | gagatgcaac | 240 |
| acaggagaaa | gatccttatc | cttactgaac | tgtgaggaga | ttaaaagcca | gtttgaaggc | 300 |
| tttgtgaagg | atataatgtt | aaacaaagag | gagacgaaga | agaaaacag | ctttgaaatg | 360 |
| caaaaaggtg | atcagaatcc | tcaaattgcg | gcacatgtca | taagtgaggc | cagcagtaaa | 420 |
| acaacatctg | tgttacagtg | ggctgaaaaa | ggatactaca | ccatgagcaa | caacttggta | 480 |
| accctggaaa | atgggaaaca | gctgaccgtt | aaaagacaag | gactctatta | tatctatgcc | 540 |
| caagtcaccct | tctgttccaa | tcgggaagct | tcgagtcaag | ctccatttat | agccagcctc | 600 |
| tgcctaaagt | cccccggtag | attcgagaga | atcttactca | gagctgcaaa | tacccacagt | 660 |
| tccgccaaac | cttgcaggca | caatccatt | cacttgggag | gagtatttga | attgtaacca | 720 |
| ggtgcttcgg | tgtttgtcaa | tgtgactgat | ccaagccaag | tgagccatgg | cactggctca | 780 |
| cgtcctttgg | cttactcaaa | ctctgaacag | tgtcaccttg | caggctgtgg | tggagctga | 839 |

<210> SEQ ID NO 3
<211> LENGTH: 1250
<212> TYPE: DNA
<213> ORGANISM: mus musculus

<400> SEQUENCE: 3

| | | | | | |
|---|---|---|---|---|---|
| ctttcagtca | gcatgataga | acatacagc | caaccttccc | ccagatccgt | ggcaactgga | 60 |
| cttccagcga | gcatgaagat | ttttatgtat | ttacttactg | ttttccttat | cacccaaatg | 120 |
| attggatctg | tgcttttttgc | tgtgtatctt | catagaagat | tggataaggt | cgaagaggaa | 180 |
| gtaaaccttc | atgaagattt | tgtattcata | aaaaagctaa | agagatgcaa | caaggagaa | 240 |
| ggatctttat | ccttgctgaa | ctgtgaggag | atgagaaggc | aatttgaaga | ccttgtcaag | 300 |
| gatataacgt | taaacaaaga | agagaaaaaa | gaaaacagct | ttgaaatgca | aagaggtgat | 360 |
| gaggatcctc | aaaattgcag | cacacgttgta | agcgaagcca | acagtaatgc | agcatccgtt | 420 |
| ctacagtggg | ccaagaaagg | atattatacc | atgaaaagca | acttggtaat | gcttgaaaat | 480 |
| gggaaacagc | tgacggttaa | aagagaagga | ctctattatg | tctacactca | agtcaccttc | 540 |
| tgctctaatc | gggagccttc | gagtcaacgc | ccattcatcg | tcggcctctg | gctgaagccc | 600 |
| agcagtggat | ctgagagaat | cttactcaag | gcggcaaata | cccacagttc | ctcccagctt | 660 |
| tgcgagcagc | agtctgttca | cttgggcgga | gtgtttgaat | acaagctgg | tgcttctgtg | 720 |
| tttgtcaacg | tgactgaagc | aagccaagtg | atccacagag | ttggcttctc | atcttttggc | 780 |
| ttactcaaac | tctgaacagt | gcgctgtcct | aggctgcagc | agggctgatg | ctggcagtct | 840 |
| tccctataca | gcaagtcagt | taggacctgc | cctgtgttga | actgcctatt | tataacccta | 900 |
| ggatcctcct | catggagaac | tatttattat | gtaccccaa | ggcacataga | gctggaataa | 960 |

-continued

```
gagaattaca gggcaggcaa aaatcccaag ggaccctgct ccctaagaac ttacaatctg    1020
aaacagcaac cccactgatt cagacaacca gaaaagacaa agccataata cacagatgac    1080
agagctctga tgaaacaaca gataactaat gagcacagtt ttgttgtttt atgggtgtgt    1140
cgttcaatgg acagtgtact tgacttacca gggaagatgc agaagggcaa ctgtgagcct    1200
cagctcacaa tctgttatgg ttgacctggg ctccctgcgg ccctagtagg               1250
```